United States Patent [19]

Dayton et al.

[11] Plant 4,633

[45] Jan. 27, 1981

[54] COOP 22

[75] Inventors: Daniel F. Dayton, Urbana, Ill.; Frank H. Emerson; Jules Janick, both of West Lafayette, Ind.; Edwin B. Williams, Lafayette, Ind.; Catherine H. Bailey, Englishtown, N.J.; James B. Mowry, Carbondale, Ill.; L. Fredric Hough, Bloomsbury, N.J.

[73] Assignee: Purdue Research Foundation, West Lafayette, Ind.

[21] Appl. No.: 70,855

[22] Filed: Aug. 29, 1979

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—John R. Nesbitt

[57] ABSTRACT

A new and distinct cultivar of apple tree which is distinctly characterized by its high fruit quality and its resistance to *Venturia inaequalis* (Cke.) Wint., the causal agent of the apple scab disease. This new variety of apple tree, now designated as COOP 22, is a seedling of known parentage planted in 1965 in the PW Breeding Orchard of the Department of Horticulture at the Illinois Agricultural Experiment Station, Urbana, Ill., which site is a cultivated area. In the above mentioned orchard, its position was Row 40, Tree 116, having the designation PRI 2016-100 in the breeding records.

After observation the selection was asexually reproduced by grafting on seedling apple roots. The grafted material has maintained the described characteristics after propagation.

1 Drawing Figure

BACKGROUND OF THE INVENTION

Figure 1:
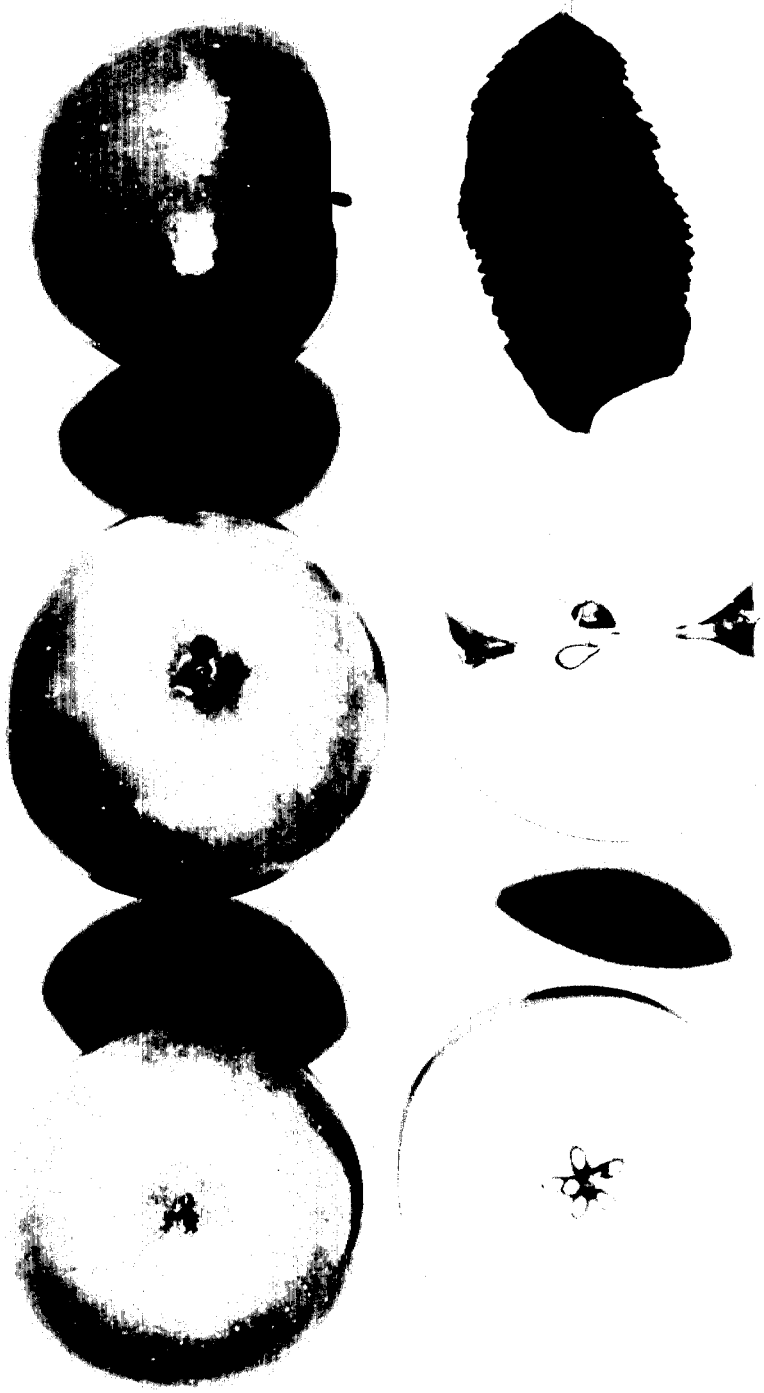
FIG. 1 is a photograph showing typical examples of fruit and foliage of COOP 22.

The present new cultivar is a seedling produced from crossing the seedling PRI 855-102 as the seed parent and New Jersey 31 as the pollen parent in 1964 at Urbana, Ill. This new cultivar carries a genetic factor, $V_f$, inherited from *Malus floribunda* 821, which causes it to be resistant to infection caused by *Venturia inaequalis*. The presence of this factor has been repeatedly proven by controlled inoculation tests in the Purdue University greenhouse of the seedling and of its offspring produced from controlled crosses. The complete pedigree is shown below:

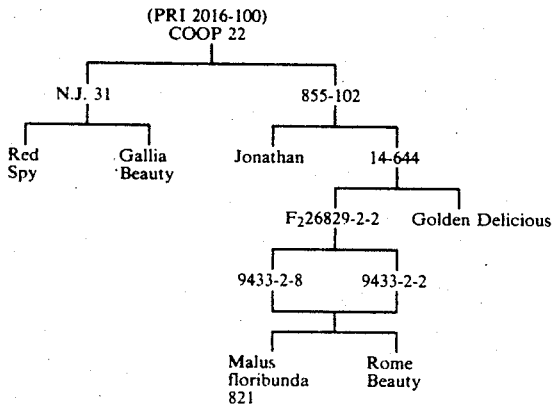

The new cultivar produces a moderately spreading and vigorous tree. The tree is productive and produces annually. It is field immune to apple scab and moderately resistant to fireblight and powdery mildew.

The tree flowers both on spurs and from axillary buds on vigorous 1-year shoots. Spur flowers open about two days earlier than 'Jonathan', while axillary flowers open up to two days later than 'Jonathan'. The apple fruit has fine dessert and culinary quality, with crisp texture and a rich sub acid flavor. Texture and flavor are maintained eight weeks or more at 34° F. There is little tendency for the fruit to drop before maturity. The fruit does not develop the "Jonathan Spot" disorder when overripe or after long storage.

DETAILED DESCRIPTION OF THE NEW VARIETY

The following is a detailed description of this new cultivar with color designations according to the 1966 Royal Horticultural Society Colour Chart, issued by the Royal Horticultural Society of London:

FLOWER

Pedicel: (Length) 1.3 cm.

Corolla: (Diameter) 3.7 cm.

Color: (Bud) red-purple, plate 61C; (open) upper side white to very pale red-purple, plate 69 D; Lower side red-purple, plate 64 D.

FRUIT

Shape: Roundish oblate to slightly conic; regular, slightly lop-sided.

Size: 6.3 to 7.6 cm (2½" to 3") diameter ×5.5 to 7.0 cm (2¼" to 2¾") long.

Color:

*Undercolor.*—Yellow-green (plate 145 C) to yellow (plate 2 C).

*Overcolor.*—75 to 95% medium to dark red (plates 45 C to 46A).

Skin: Smooth with dry wax with small to medium light tan dots; dots sunken or flush with surface; skin thin, tough; no overall russeting.

Stem: Average 2.0 cm, with average of 25% of its length extending below shoulders of the fruit; medium thickness and medium stiffness; stem inserted in cavity vertically or at only a very slight angle.

Cavity: Acute, deep, medium width, not russeted.

Basin: Abrupt, medium depth and width.
Calyx: Persistant, closed, lobes erect or slightly recurved.
Calyx tube: Urn shaped, closed.
Stamens: Median.
Core lines: Clasping, turbinate.
Core: Median, closed, small.
Carpels: Ovate, mucronate, smooth.
Seeds: Acute, not tufted.
Flesh:
*Texture.*—Fine grained, very crisp and slightly tough until full ripe.
*Color.*—Light yellow (plate 13D).
*Quality.*—Very good, sub acid, moderately rich flavor.
*Aroma.*—Slight, pleasant.
Maturity season: With Jonathan.
Storage characteristics: Retains excellent texture and flavor eight to ten weeks at 34° F.
Use: Very good dessert and culinary apple.

TREE AND FOLIAGE

Growth habit: Semi-spreading.

Bark: Medium brown on 1-year shoots, light brown on 2-year and older branches; surfaces relatively smooth with prominent light tan lenticels; surface of new shoots heavily pubescent.
Leaf color: Dark green, healthy.
Leaf shape: Simple, not lobed, elliptic with compound serrate margins; marginal serrations blunt to slightly rounded on vigorous shoots; marginal serrations acute on spur leaves and those on weak shoots; leaf tips acuminate, bases acute.
Aspect: Leaves on vigorous shoots: upper surface slightly rugose; leaves on spurs and weak shoots: upper surface smooth; all leaves heavily pubescent.

Size: Length-width ratio is 1.7:1.
Petiole: 1.9 to 2.6 cm in length, medium thickness, pubescent.

What is claimed is:

1. A new and distinct apple tree substantially as shown and described, particularly characterized by resistance to apple scab, excellent flesh quality and texture, and maturing approximately with 'Jonathan'.

* * * * *